(12) United States Patent
Iwaki (10) Patent No.: US 6,512,238 B1
(45) Date of Patent: Jan. 28, 2003

(54) METHOD AND APPARATUS FOR IMAGE READING CAPABLE OF DETECTING SCRATCHES OR FOREIGN MATTER ON FILM

(75) Inventor: Yasuharu Iwaki, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/480,655

(22) Filed: Jan. 11, 2000

(30) Foreign Application Priority Data

Jan. 11, 1999 (JP) .......................................... 11-003742

(51) Int. Cl.$^7$ .............................................. G01N 21/86
(52) U.S. Cl. .............................. 250/559.4; 250/559.02; 250/559.42
(58) Field of Search ........................ 250/559.01–559.03, 250/559.07, 559.08, 559.16–559.18, 559.42, 559.41, 559.46, 559.45; 356/424–431; 348/96–99, 125–131

(56) References Cited

U.S. PATENT DOCUMENTS 5,220,178 A * 6/1993 Dreiling et al. ......... 250/559.03

* cited by examiner

Primary Examiner—Frank G. Font
Assistant Examiner—Thanh X. Luu
(74) Attorney, Agent, or Firm—Birch, Stewart, Kolasch & Birch, LLP (57) ABSTRACT

An image reading method and apparatus allow reading light to be incident on a film to obtain projected light and read the thus obtained projected light photoelectrically to perform reading of an image recorded on the film. In the method and apparatus, at least one of a scratch and a foreign matter on the film is detected based on two respective reading results obtained using types of reading light in different states of diffusion such as a parallel light and a perfectly diffused light from two light sources, respectively. The method and apparatus are capable of surely detecting a scratch on the film, or dirt or foreign matter adhered to the film and correcting it as required, whereupon high-quality images having no image deterioration due to the scratch, the dirt or foreign matter can be reproduced in a consistent manner.

16 Claims, 5 Drawing Sheets

METHOD AND APPARATUS FOR IMAGE READING CAPABLE OF DETECTING SCRATCHES OR FOREIGN MATTER ON FILM

BACKGROUND OF THE INVENTION

This invention relates to an image reading method and apparatus that are used to read images recorded (photographed) on a photographic film photoelectrically. More specifically, the invention relates to an image reading method and apparatus having higher capability of detecting a scratch, a foreign matter such as dirt or dust and so forth that exist on the film, thereby obtaining image data in which the detected scratch and foreign matter have been corrected.

Heretofore, the images recorded on photographic films such as negative films and reversal films (which are hereinafter referred to simply as "films") have been commonly printed on light-sensitive materials (photographic paper) by means of direct (analog) exposure in which the film image is projected onto the light-sensitive material to achieve its areal exposure.

A new technology has recently been introduced and this is a printer that relies upon digital exposure. Briefly, the image recorded on a film is read photoelectrically, converted to digital signals and subjected to various image processing schemes to produce image data for recording purposes; recording light that has been modulated in accordance with the image data is used to scan and expose a light-sensitive material to record a latent image, which is subsequently developed to produce a (finished) print. The printer operating on this principle has been commercialized as a digital photoprinter.

In the digital photoprinter, images are converted to digital image data which are processed to determine the exposing conditions for printing. Hence, the digital photoprinter is capable of performing effective image processing operations such as the correction of washed-out highlights or flat shadows due to the taking of pictures with back light or an electronic flash, sharpening and the correction of color or density failure and this enables the production of high-quality prints that have been impossible to attain by the conventional direct exposure technique. In addition, not only the assembling of plural images and the dividing of a single image but also the compositing of characters on image can be performed by processing the image data and, as a result, prints can be output after various editing and/or processing operations have been performed in accordance with specific uses.

Outputting images as prints (photographs) is not the sole capability of the digital photoprinter; the image data can be supplied into a computer or the like and stored in recording media such as a floppy disk; hence, the image data can be put to various non-photographic uses.

Having these features, the digital photoprinter is basically composed of an image input machine having a scanner (image reading apparatus) that reads the image on a film photoelectrically and an image processing apparatus that processes the image read with the scanner to produce output image data (exposing conditions) as well as an image output machine having a printer (image recording apparatus) that scan exposes a light-sensitive material in accordance with the image data output from the image input machine to record a latent image and a processor (developing apparatus) that performs development and other necessary processing on the exposed light-sensitive material to produce a print.

In the scanner, reading light issuing from a light source is allowed to be incident on a film, from which projected light bearing the image recorded on the film is produced and focused by an imaging lens to form a sharp image on an image sensor such as a CCD sensor; the image is then read by photoelectric conversion and sent to the image processing apparatus as image data for the film (i.e., image data signals) after being optionally subjected to various image processing schemes.

In the images processing apparatus, image processing conditions are set on the basis of the image data read with the scanner and image processing as determined by the thus set conditions is performed on the read image data and the resulting output image data for image recording (i.e., exposing conditions) are sent to the printer.

In the printer, if it is of a type that relies upon exposure by scanning with an optical beam, the latter is modulate din accordance with the image data sent from the image processing apparatus and deflected in a main scanning direction as the light-sensitive material is transported in an auxiliary scanning direction perpendicular to the main scanning direction, whereby a latent image is formed as the result of exposure (printing) of the light-sensitive material with the image bearing optical beam. Development and other processing as determined by the light-sensitive material are then performed to produce a print (photograph) reproducing the image that was recorded on the film.

It is natural that the original of a print to be produced or the film must be in a good condition in order to reproduce a high-quality image thereon.

The film is transported in a camera for photographing, a developing apparatus for development and a scanner for reading (printing). During the transport, the surfaces of the film are in sliding contact with support members of the camera, the developing apparatus or the scanner. As a result, scratches may be often caused on both sides of the film. Further, the film is very often treated in an ordinary environment in which any particular air cleaning is not performed. Hence, any foreign matter such as dirt or dust is likely to adhere to the surfaces thereof.

As described above, when reading the image recorded on the film in the scanner, reading light is allowed to be incident on the film to produce projected light that is read photoelectrically with the CCD sensor. In this process, any foreign matter adhered to the film surfaces or any damage thereof blocks out or diffuses the reading light (projected light) to thereby reduce the quantity of light. In case of a deep scratch, the quantity of transmitted light of the reading light is increased to the contrary, whereby the light intensity of the projected light incident on the CCD sensor becomes inappropriate and no longer corresponds to the image on the film.

As a result, a high quality image cannot be obtained, since the foreign matter or the scratch is reproduced like a shadow on the obtained image and the peripheral image portion of the scratch looks blurred on the obtained image.

SUMMARY OF THE INVENTION

A primary object of the present invention is to solve the prior art problems by providing an image reading method that is applied to the aforementioned digital photoprinter and that is capable of surely detecting a foreign matter such as dirt or dust adhered to the film and a scratch thereon as will as an image reading apparatus used in the digital photoprinter for implementing the above method.

Another object of the invention is to provide an image reading method and apparatus that ensure correction of the detected scratch and foreign matter thereby obtaining image data capable of reproducing a high quality image without deterioration due to the scratch and the foreign matter, as in the primary object of the invention described above.

In order to achieve the above objects, the present invention provides an image reading method comprising the steps of:

allowing reading light to be incident on and pass through a film to obtain projected light; and reading the thus obtained projected light photoelectrically to perform reading of an image recorded on the film, wherein at least one of a scratch and a foreign matter on the film is detected based on at least two reading results obtained by reading the same image independently with at least two types of reading light in different states of diffusion.

Preferably, the at least two types of reading light in the different states of diffusion include a type of reading light in a state near to parallel light and another type of reading light in a state near to perfectly diffused light.

Preferably, the scratch and the foreign matter are a scratch and a foreign matter in the image or an image area recorded on the film.

Preferably, the at least two types of reading light in the different states of diffusion include reading types of light that are issued from at least two light sources and in which the states of diffusion are different from each other.

Preferably, the at least two types of reading light in the different states of diffusion include a type of reading light issued from a light source and another type of reading light obtained by diffusing the type of reading light issued from the light source by means of a diffusing device so that the states of diffusion are different from each other.

Preferably, the at least two reading results are obtained by using a plurality of sensors having different spectral sensitivities in accordance with the states of diffusion of the at least two types of reading light in the different states of diffusion.

The present invention also provides an image reading apparatus which allows reading light to be incident on and pass through a film to obtain projected light and reads the thus obtained projected light photoelectrically to perform reading of an image recorded on the film, comprising:

a light-issuing device for allowing at least two types of reading light in different states of diffusion to be incident on the film;

an image reading device for reading photoelectrically the projected light bearing the image recorded on the film as obtained from the at least two types of reading light in the different states of diffusion that have been issued from the light-issuing device and passed through the film; and a detecting device for detecting at least one of a scratch and a foreign matter on the film based on at least two reading results obtained by reading the same image independently with the at least two types of reading light in the different states of diffusion by means of the image reading device.

Preferably, the light-issuing device includes at least two light sources that issue the at least two types of reading light in the different states of diffusion, respectively.

Preferably, the light-issuing device includes a light source issuing a type of reading light and a changing device for changing the type of reading light issued from the light source so that said states of diffusion of said type of reading light and another type of reading light being produced are different from each other.

Preferably, the image reading device has a plurality of sensors having different spectral sensitivities and the plurality of sensors having the corresponding spectral sensitivities are used in accordance with the states of diffusion of the at least two types of reading light in the different states of diffusion to obtain the at least two reading results.

Preferably, one of the plurality of sensors is a monochrome sensor.

Preferably, the image reading device obtains the at least two reading results by prescan for reading the image recorded on the film at low resolution.

Preferably, the detecting device uses the at least two reading results to detect, as the at least one of the scratch and the foreign matter, a region that has a difference between image data read with reading light of lower diffusion and image data read with reading light of higher diffusion in the at least two types of reading light in the different states of diffusion.

Preferably, the image reading apparatus further includes a deficient pixel correcting device for correcting, as deficient pixels, a region corresponding to the at least one of the scratch and the foreign matter detected by the detecting device.

Preferably, the deficient pixel correcting device performs correction using surrounding image data of the deficient pixels.

Preferably, the deficient pixel correcting device performs at least one of a method of substituting image data of the deficient pixels by the surrounding image data of the deficient pixels, a method of substituting the image data of the deficient pixels by image data calculated by interpolation with the surrounding image data of the deficient pixels, and a method of using, as the image data of the deficient pixels, image data read with reading light of higher state of diffusion in the at least two types of reading light in the different states of diffusion.

DETAILED DESCRIPTION OF THE INVENTION

The image reading method and apparatus of the invention are now described in detail with reference to the preferred embodiments shown in the accompanying drawings.

Figure 1:
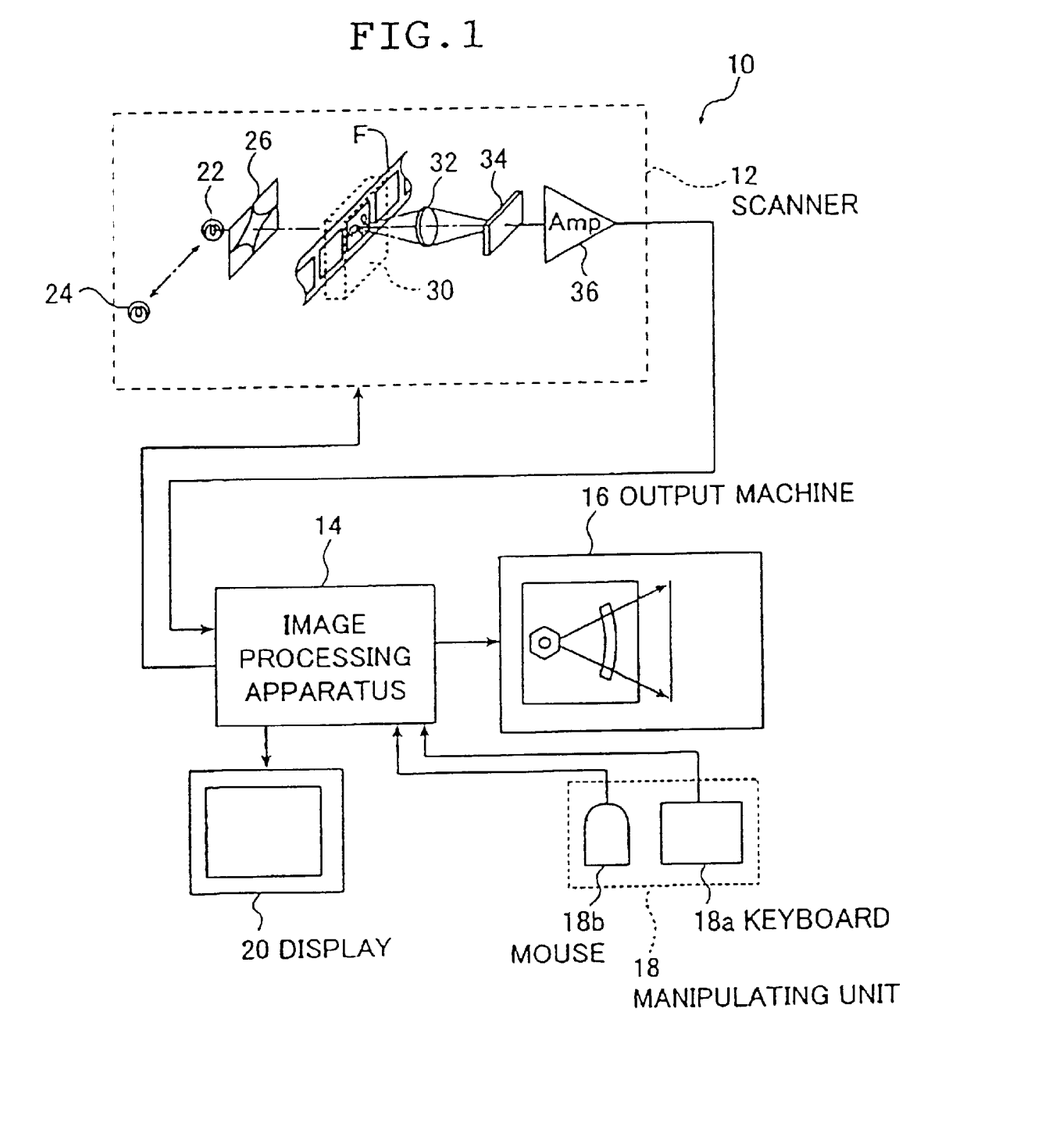
FIG. 1 is a block diagram of a photoprinter using the image reading apparatus according to an embodiment of the invention.

FIG. 1 is a block diagram of an exemplary digital photoprinter using the image reading apparatus according to an embodiment of the invention (which is hereinafter referred to simply as "photoprinter").

The photoprinter 10 shown in FIG. 1 is basically composed of an image input machine having a scanner (image reading apparatus) 12 for photoelectrically reading the image recorded on a film F, and an image processing apparatus 14 which performs image processing on the image data (image information) read with the scanner 12 and with which the photoprinter 10 as a whole is manipulated and controlled, as well as an image output machine 16 which performs imagewise exposure of a light-sensitive material (photographic paper) with light beams modulated in accordance with the image data delivered from the image processing apparatus 14 and which performs development and other necessary processing to produce a (finished) print.

Connected to the image processing apparatus 14 are a manipulating unit 18 including a keyboard 18a and a mouse 18b for inputting (setting) various conditions, selecting and commanding a specific processing step and entering a command and so forth for effecting color/density correction, as well as a display 20 for representing the image read with the scanner 12, various manipulative commands and pictures for setting and registering various conditions.

The scanner 12 forms the image reading apparatus for implementing the image reading method of the invention. It is an apparatus with which the images recorded on the film F are read photoelectrically frame by frame. It comprises a first light source 22, a second light source 24, a variable diaphragm 26, an imaging lens unit 32, an image sensor 34 having line CCD sensors capable of reading R (red), G (green) and B (blue) images, and an amplifier (Amp) 36.

In the photoprinter 10, dedicated film carriers 30 are available that can be loaded into the housing of the scanner 12 in accordance with the type or size of the film used (e.g. whether it is a film of the Advanced Photo System (APS) or a negative or reversal film of 135 size), the format of the film (e.g. whether it is a strip or a slide) or other factor. By replacing one carrier with another, the photoprinter 10 can be adapted to process various kinds of films in various modes. The images (frames) that are recorded on the film and which are subjected to the necessary procedure for print production are transported to and held in a specified reading position by means of the film carriers 30.

As is well known, magnetic recording media are preliminarily formed on the film F and APS to record various kinds of information including cartridge ID number and film type. When shooting or developing, various data including the date of shooting or development, camera type and developing machine type can be recorded. The film carrier 30 adapted for the APS film (cartridge) is provided with a device for reading the magnetic information, which is read during transport of the film F to the reading position and the thus read information is sent to the image processing apparatus 14 together with the various kinds of information described above.

The scanner 12 reads the images recorded on the film F in the following manner; the reading light from the first light source 22 has its quantity adjusted by means of the variable diaphragm 26 and is vertically incident on the film F held in the specified reading position by means of the film carrier 30 and thereafter passes through the film F to produce projected light bearing the image recorded on the film F. It should be noted that the first and second light sources 22 and 24 are not limited in any particular way, if the reading lights issuing from the two light sources 22 and 24 have different states of diffusion. Then, various known light sources for use in photoelectric image reading as exemplified by a halogen lamp are available.

The film carrier 30 is adapted for a web of the film F (strip) such as a 24-exposure film of 135 size or APS cartridge. As shown schematically in FIG. 2A, the film carrier 30 has transport roller pairs 30a and 30b, and a mask 25 having a slit 25a. The transport roller pairs 30a and 30b are provided on opposite sides of the specified reading position in an auxiliary scanning direction which is perpendicular to the main scanning direction (i.e., the direction in which the line CCD sensors in the image sensor 34 extend) and they transport the film F with its length being parallel to the auxiliary scanning direction as it is in registry with the reading position. The slit 25a defines the projected light from the film F to have a specified narrow shape, is in registry with the reading position and extends in the main scanning direction.

Figure 2A:
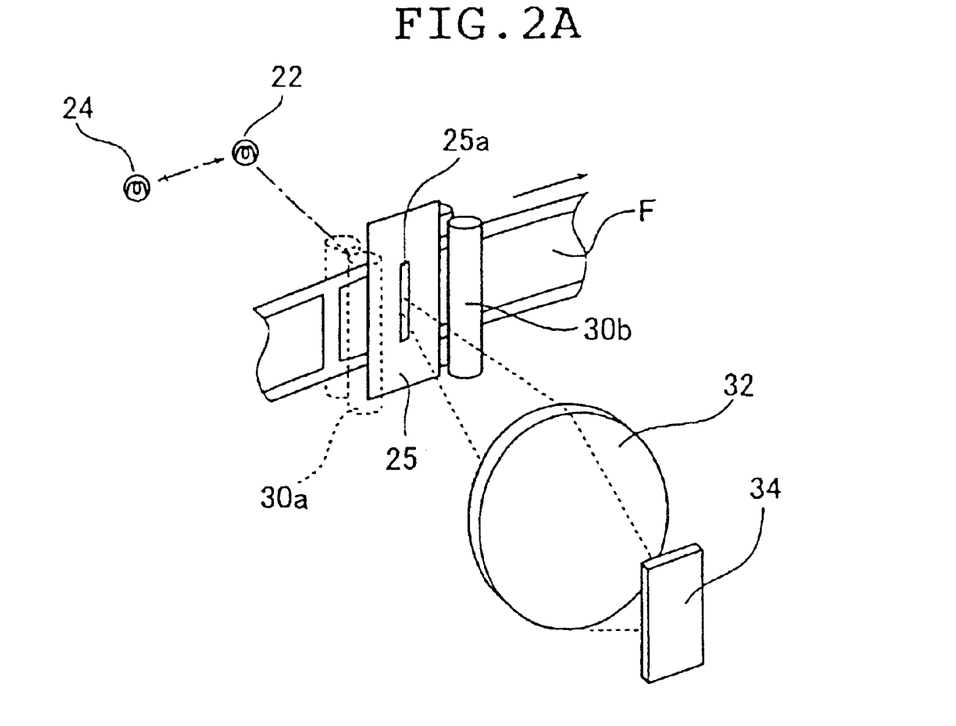
FIG. 2A is a perspective view that shows diagrammatically a film scanner to be mounted on the photoprinter shown in FIG. 1.

The film F is set so as to pass through the reading position by the film carrier 30 and transported in the auxiliary scanning direction. The reading light is incident on the film F in the reading position. Consequently, the film F is subjected to two-dimensional slit scan with the reading light passing through the slit 25a extending in the main scanning direction, whereupon the image of each frame recorded on the film F is captured.

The projected light from the film F is focused by the imaging lens unit 32 to form a sharp image on the light-receiving plane of the image sensor 34.

Figure 2B:
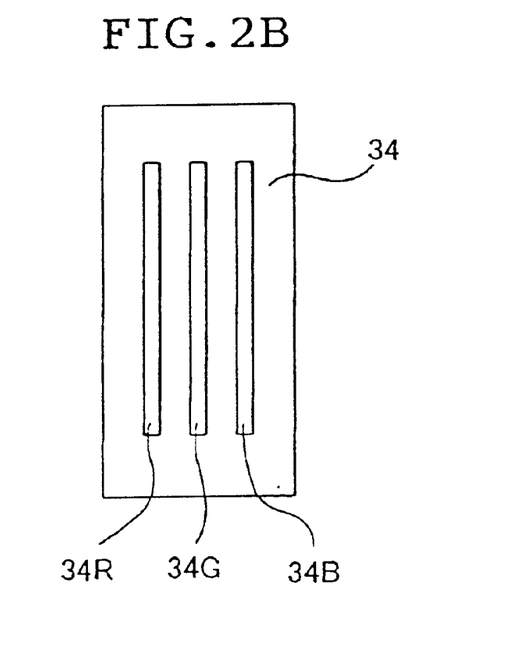
FIG. 2B is a conceptual view showing an image sensor in the photoprinter shown in FIG. 1.

As shown in FIG. 2B, the image sensor 34 is a so-called 3-line color CCD sensor comprising a line CCD sensor 34R for reading a R image, a line CCD sensor 34G for reading a G image, and a line CCD sensor 34B for reading a B image. As already mentioned, the respective line CCD sensors extend in the main scanning direction. The projected light from the film F is separated into three primary colors R, G and B and read photoelectrically by means of the image sensor 34.

The output signals from the image sensor 34 are amplified with the amplifier 36 and sent to the image processing apparatus 14.

In the scanner 12, the images recorded on the film F are read with the first light source 22 by two scans, the first being prescan at low resolution and the second being fine scan for obtaining output image data.

In the scanner 12 according to the invention, prescan is followed by another reading with the second light source 24 that is performed to detect a scratch on the film F or a foreign matter such as dirt or dust adhered to the film F. This reading due to the second light source 24 is hereinafter referred to as "second prescan" and the prescan due to the first light source 22 may be hereinafter referred to as "first prescan" for the sake of convenience.

The second light source 24 described above is interchanged with the first light source 22 in the position in which the latter is located. The difference between the two sources is that the state of diffusion of the reading light issued from the first light source 22 is near to that of parallel light, whereas that of the reading light issued from the second light source 24 near to that of perfectly diffused light. In the illustrated scanner 12, after the end of the first prescan, photoelectric reading in the second prescan due to the second light source 24 is performed in quite the same manner as in the first prescan except that the first light source 22 is replaced by the second light source 24.

The illustrated scanner 12 does not have a variable diaphragm for the second light source 24. In the present invention however, a variable diaphragm may also be provided as required for the second light source 24. The quantity of light of the reading light may be optionally changed between the first prescan and the second prescan.

Changeover between the first light source 22 in the first prescan and the second light source 24 in the second prescan is performed by a changeover unit (not shown). The changeover unit has an interchange device for interchanging the first light source 22 with the second light source 24 and vice versa, and a power supply switching device that turns on and off the two light sources 22 and 24. The interchange device for interchanging the first light source 22 with the second light source 24 and vice versa may be omitted, if the second light source 24 issuing the reading light of which the state of diffusion is near to that of the perfectly diffused light can be located in proximity to the first light source 22 issuing the reading light of which the state of diffusion is near to that of the parallel light, and if the positional shift of the second light source 24 from the first light source 22 can be ignored in image reading.

As already mentioned, the output signals (image data) from the scanner 12 are output to the image processing apparatus 14 (which is hereinafter simply referred to as "processing apparatus 14").

Figure 3:
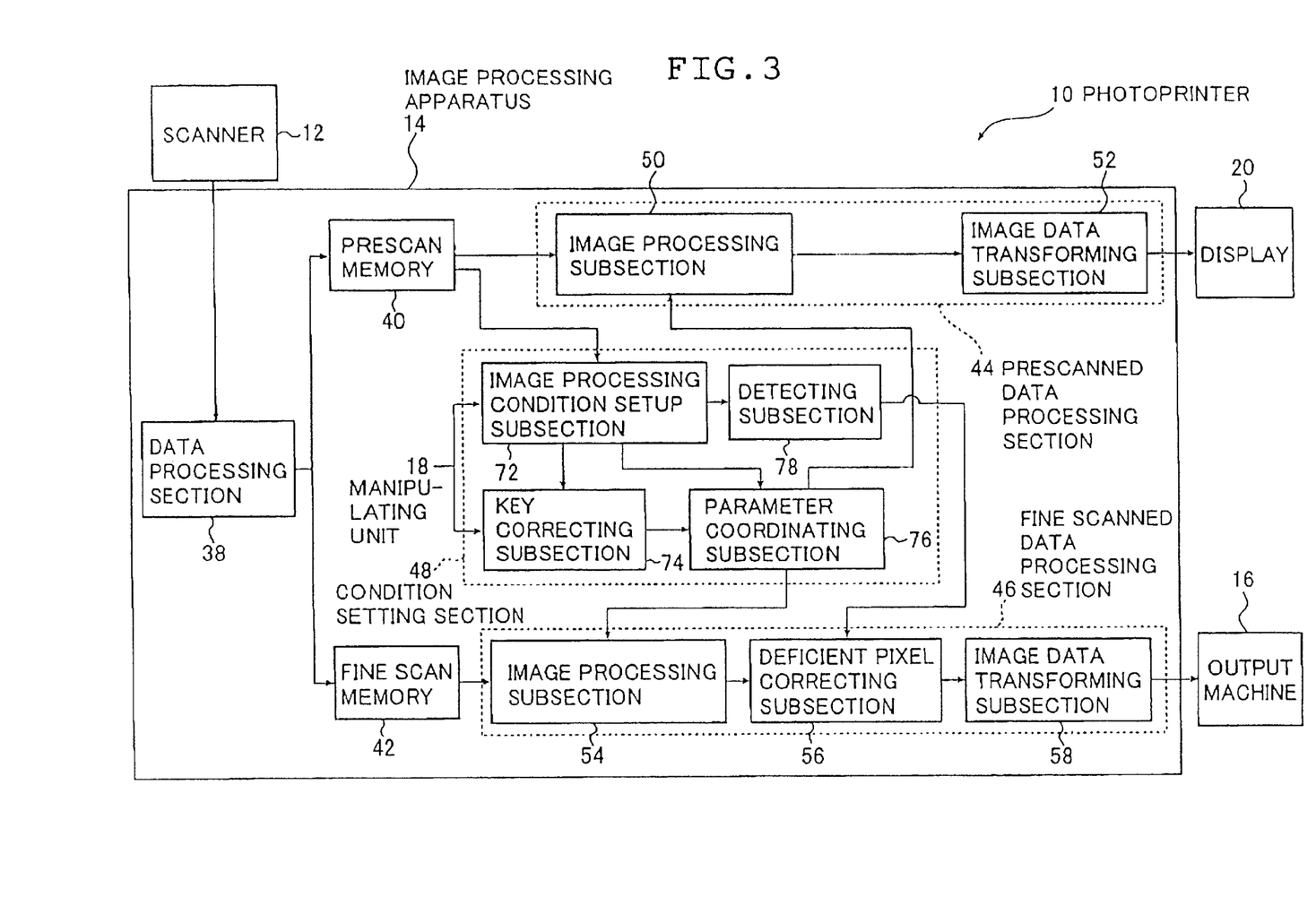
FIG. 3 is a block diagram showing an image processing apparatus in the photoprinter shown in FIG. 1.

FIG. 3 is a block diagram of an embodiment of the processing apparatus 14. The processing apparatus 14 comprises a data processing section 38, a prescan (frame) memory 40, a fine scan (frame) memory 42, a prescanned data processing section 44, a fine scanned data processing section 46 and a condition setting section 48.

FIG. 3 shows only the parts related to image processing and besides these parts, the processing apparatus 14 includes a CPU for controlling and managing the overall operation of the photoprinter 10 including the processing apparatus 14, and memories for storing the information necessary for the operation and otherwise of the photoprinter 10. The manipulating unit 18 and the display 20 are connected to related parts via the CPU and the like (CPU bus).

The R, G and B output signals from the scanner 12 are respectively sent to the data processing section 38, where they are subjected to specified steps such as analog/digital (A/D) conversion, Log conversion, DC offset correction, dark correction and shading correction to generate digital image data, of which prescanned (image) data (which is also hereinafter simply referred to as "first prescanned data") and second prescanned data are stored in the prescan memory 40 and fine scanned (image) data is stored in the fine scan memory 42.

It should be noted that the output signals for the first and second prescans, and the fine scan are essentially the same data except for the resolution and output signal level.

The prescanned data stored in the prescan memory 40 is processed in the prescanned data processing section 44 that comprises an image processing subsection 50 and an image data transforming subsection 52.

The fine scanned data stored in the fine scan memory 42 is processed in the fine scanned data processing section 46 that comprises an image processing subsection 54, a deficient pixel correcting subsection 56 and an image data transforming subsection 58.

The image processing subsection 50 in the prescanned data processing section 44 and the image processing subsection 54 in the fine scanned data processing section 46 are the sites where the image (image data) read with the scanner 12 is subjected to specified image processing schemes in accordance with the image processing conditions that are set by means of the condition setting section 48 to be described later in this specification. The two image processing subsections 50 and 54 perform basically the same processing except for the resolution.

The image processing schemes to be performed in the image processing subsections 50 and 54 are not limited in any particular way, and include various image processing performed in known image processing apparatuses, as exemplified by color balance adjustment, tonal adjustment, density adjustment, chroma adjustment, electronic magnification, dodging (compressing/extending the density's dynamic range) and sharpening. These schemes are performed by known methods by means of processing with look-up tables (LUTs), matrix (MTX) computing units, low-pass filters, adders and so forth, or appropriate combinations thereof for averaging and interpolation.

The deficient pixel correcting subsection 56 of the fine scanned data processing section 46 is the site in which pixels corresponding to the region having a scratch or foreign matter on the film F (hereinafter referred to as "deficient pixels") as detected by the condition setting section 48 (detecting subsection 78) to be described below are corrected to obtain image data in which the scratch or foreign matter on the film P has been corrected.

The method of correcting the deficient pixels is not limited in any particular way and any known methods are available. An exemplary method is to correct the deficient pixels using the image data of the surrounding pixels of the deficient pixels. Specific methods include a method of substituting the image data of the deficient pixels by those of the surrounding pixels, and a method in which the image data of the deficient pixels are calculated by interpolation with those of the surrounding pixels and the thus obtained image data are used. Alternatively, the deficient pixels may be corrected by using, as the image data of the deficient pixels, the image data red by the reading light in a higher state of diffusion, more preferably in a state near to that of the perfectly diffused light, for example the second prescanned data in this case. This is because the portions of the scratch and the foreign matter on the image read by the reading light in the high state of diffusion are blurred to make them less marked, as described below.

The image data transforming subsection 58 transforms the image data processed in the image processing subsection 54 using three-dimensional (3D) LUTs and the like and supplied to the image output machine 16 as image data suitable for image recording with the image output machine 16.

The image data transforming subsection 52 also uses 3D LUTs and the like to transform the image data processed in the image processing subsection 50 into image data corresponding to the representation on the display 20, after optionally thinning out. The transformed data is then represented on the display 20.

The condition setting section 48 sets the conditions for various processing schemes to be performed with the image processing subsections 50, 54 and detects the deficient pixels to be corrected in the deficient pixel correcting subsection 56, that is, any scratch or foreign matter on the film F.

The condition setting section 48 comprises an image processing condition setup subsection 72, a key correcting subsection 74, a parameter coordinating subsection 76 and a detecting subsection 78. It should be noted that the condition setting section 48 sets not only the image processing conditions but also the reading condition for fine scan. For example, the quantity of light of the first light source 22, the stop-down value of the variable diaphragm 26 and the storage time of the image sensor 34 are set from the prescanned data so that the line CCD sensors are saturated at a slightly lower density than the minimum density of the image of interest.

The image processing condition setup subsection 72 (hereinafter referred to as "setup subsection") uses the prescanned data to set (or calculate) the conditions for the various image processing schemes to be performed in the image processing subsection 54 (50) and supplies the thus set conditions to the parameter coordinating subsection 76.

Specifically, the setup subsection 72 reads the prescanned data out of the prescan memory 40 to perform various operations including the construction of density histograms and the calculation of various image characteristic quantities such as average density, LATD (large-area transmission density), highlights (minimum density) and shadows (maximum density); in accordance with such density histograms and image characteristic quantities and an instruction by the operator, the setup subsection 72 sets the conditions for various image processing schemes including color balance adjustment and tonal adjustment as described above.

The key correcting subsection 74 calculates the amounts for adjusting the image processing conditions such as correcting amount of LUTs in accordance with various commands for adjustment entered by means of a density (brightness) adjustment key, color adjustment keys, a contrast adjustment key, a sharpness adjustment key and a chroma adjustment key, all being set on the keyboard 18*a*, as well as by means of the mouse 18*b*; the thus calculated amounts are supplied to the parameter coordinating subsection 76.

After receiving the image processing conditions set by the setup subsection 72, the parameter coordinating subsection 76 sets the supplied image processing conditions in the image processing subsection 50 of the prescanned data processing section 44 and the image processing subsection 54 of the fine scanned data processing section 46; further, in accordance with the amounts of adjustment as calculated by the key correcting subsection 74, the parameter coordinating subsection 76 corrects (adjusts) the image processing conditions set in various parts or makes another setting of the image processing conditions.

The first prescanned data and the second prescanned data stored in the prescan memory 40 are supplied from the setup subsection 72 to the detecting subsection 78.

The detecting subsection 78 is the site in which a scratch formed on the film F and a foreign matter such as the dirt, the dust or the stain adhered to the film F are detected by means of the first prescanned data and the second prescanned data, after which the deficient pixels are detected based on the results obtained.

Figure 4A:
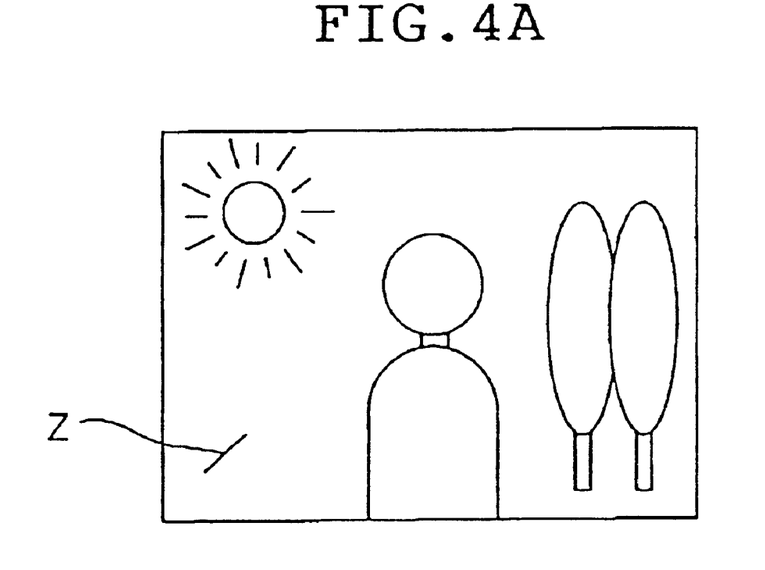
FIG. 4A is a conceptual view illustrating a method of detecting a scratch or foreign matter in the image reading apparatus according to the above embodiment.

When a frame of the film F has a scratch 2 as shown in FIG. 4A schematically, in first prescan mode using the first light source 22 that issues the substantially parallel light as the reading light and makes it incident on the film F substantially at right angles therewith, projected light (reading light) from the film F is adversely affected by the scratch Z to generate image data in which the scratch Z is relatively sharpened. (In general, the output from the image senor 34 is reduced in the portion having the scratch Z, as described below.)

Figure 4B:
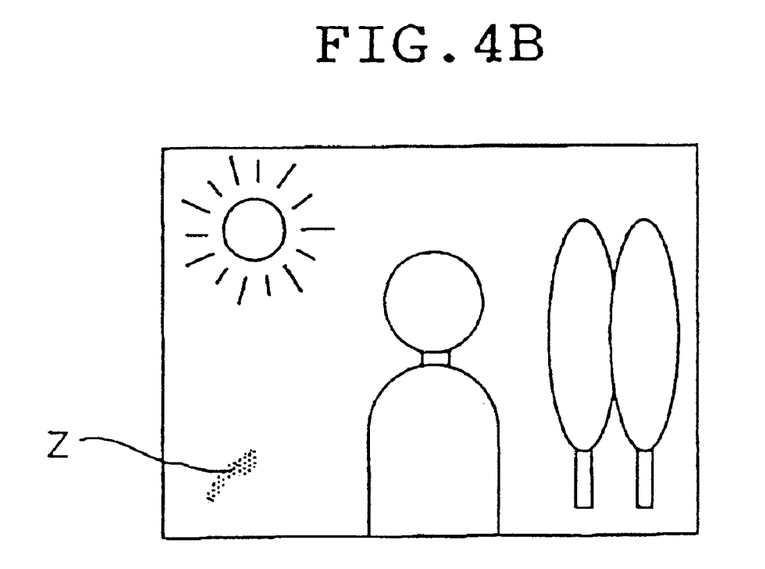
FIG. 4B is a conceptual view illustrating another detecting method in the image reading apparatus according to the above embodiment.

On the other hand, when performing image reading in second prescan mode in the same manner used the second light source 24 that issues the substantially perfectly diffused light as the reading light incident on the film F, if the scratch Z is on the film F, the reading light from the second light source 24 is further scattered by the scratch Z before being incident on the image sensor 34. Therefore, in the image data obtained by the second prescan, the scratch Z is read as a blurred image, as schematically shown in FIG. 4B.

Further, if the scratch on the film F is a slight one due to sliding contact with any components, the quantity of transmitted light is reduced because the projected light is scattered in the portion including the scratch. The image data obtained by the first prescan has higher (darker) density in the position corresponding to the scratch than on the periphery thereof. If the scratch is so deep as to exceed the emulsion layer (image forming layer) of the film F to the contrary, the quantity of transmitted light is increased, and the image data obtained by the first prescan has lower (brighter) density in the position corresponding to the scratch than on the periphery thereof.

In contrast, in the second prescan using the second light source 24, the reading light is scattered by the scratch irrespective of the degree of the scratch on the film F, and the scratch is read as blurred image as described above.

When a foreign matter has been attached to a frame of the film F, in the first prescan mode using the first light source 22 that issues the substantially parallel light as the reading light and makes it incident on the film F substantially at right angles therewith, projected light (reading light) from the film F is blocked out by the foreign matter. Therefore, the image data in the position corresponding to the foreign matter has a higher density than the peripheral image data (the output from the image sensor 34 is reduced).

On the other hand, in the second prescan mode using the second light source 24 that issues the substantially perfectly diffused light as the reading light, the reading light of the substantially perfectly diffused state from the second light source 24 is further scattered by the foreign matter on the film F before being incident on the image sensor 34. Therefore, in the image data obtained by the second prescan, the foreign matter is read as a blurred image, as same as the scratch described above.

The detecting subsection 78 detects the deficient pixels by means of the first prescanned image data and the second prescanned image data. If a region of the first prescanned image data has no continuity with the surrounding pixels and has abruptly a higher or lower density than the surrounding pixels, and if the region has a smooth output change corresponding to the blurred image in the second prescanned image, the detecting subsection 78 judges the film F has a scratch or foreign matter in this region, and the corresponding pixels are regarded as the deficient pixels. This information is then sent to the deficient pixel correcting subsection 56.

The deficient pixel correcting subsection 56 corrects accordingly the deficient pixels using the surrounding pixels, as described above.

We now describe the image reading apparatus of the invention in greater detail by explaining the operations of the scanner 12 and the processing apparatus 14.

The operator loads the scanner 12 with the film carrier 30 that is associated with the film F (or frame to be read), sets the film F in a specified position on the film carrier 30, enters the necessary information such as the size of the prints to be prepared and finishing information, and thereafter keys in a command for starting print preparation.

In response to the START command, the stop-down value of the variable diaphragm 26 in the scanner 12 and the storage time of the image sensor (line CCD sensors) 34 are set in accordance with the reading conditions for prescan; thereafter, the film carrier 30 transports the film F in the auxiliary scanning direction at a specified speed adapted for prescan to start prescan; as already mentioned, the film F is subjected to slit scan and the projected light is focused on the image sensor 34 so that the image recorded on the film F is read photoelectrically as R, G and B separations. The thus read image data is output to and stored in the prescan memory 40.

In this embodiment, first prescan, second prescan and fine scan are performed in an example frame by frame. However, this is not the sole case of the invention, and all frames or frame groups each consisting of a given number of frames may successively be subjected to the first prescan, the second prescan and the fine scan, before being subjected for each frame to image processing as described below.

After the end of the first prescan, the second prescan is performed in the same manner as the first prescan, except that the film carrier 30 transports the film F in the reverse direction and the first light source 22 is replaced by the second light source 24. The second prescanned data is also stored in the prescan memory 40.

When the prescan memory 40 stores the first prescanned data, the setup subsection 72 in the condition setting section 48 reads the stored first prescanned data out of the prescan memory 40, constructs density histograms, calculates image characteristic quantities such as highlights and shadows and performs any other necessary operations on a frame-by-frame basis to set the reading conditions for the fine scan of successive frames. The setup subsection 72 further sets the image processing conditions for each frame including extraction of the frame position of each frame, construction of tonal adjustment table and gray balance adjustment table, construction of MTX operations for chroma correction, and supplies the thus set conditions to the parameter coordinating subsection 76.

Upon receiving the image processing conditions, the parameter coordinating subsection 76 sets them at specified sites (hardware) in the image processing subsection 50 of the prescanned data processing section 44 and in the image processing subsection 54 of the fine scanned data processing section 46.

When the prescan memory 40 also stores the second prescanned data, the latter is read by the setup subsection 72 and sent to the detecting subsection 78 together with the first prescanned data.

The detecting subsection 78 uses the delivered first and second prescanned data to detect the region in which the first prescanned data shows an abrupt change as compared with the periphery and the second prescanned data shows a smooth output change corresponding to the blurred image. The corresponding pixels are output to the deficient pixel correcting subsection 56 of the fine scanned data processing section 46 as the deficient pixels.

According to the present invention, the system may also be adapted to give an alarm or represent on the display 20 when the detection subsection 78 detected the deficient pixels, thereby informing the operator that the film F has a scratch or foreign matter.

When verification is to be performed, the prescanned data is read out of the prescan memory 40 by the prescanned data processing section 44 and subjected to image processing under the image processing conditions previously set in the image processing subsection 50. Then, the processed data is converted in the image data transforming subsection 52 and represented on the display 20 as the simulation image.

For example, the detection results of the deficient pixels by the detecting subsection 78 may also be output to the image data transforming subsection 52 so that the subsection 52 can process the image data in accordance with the obtained detection results to represent the position of the scratch or foreign matter on the display 20 in a noticeable manner by coloring with a specified color or enhancing the brightness. Thus, the operator can easily detect the position thereof.

Looking at the simulation image being represented on the display 20, the operator performs verification of the image or processing results, and as required, performs color, density or gradation adjustment using adjustment keys on the keyboard 18a.

The thus entered command for adjustment is sent to the key correcting subsection 74, where the amounts for correcting the image processing conditions are calculated in accordance with various commands entered for adjustment. The calculated amounts are then sent to the parameter coordinating subsection 76, where the LUTs and MTXs in the image processing subsections 50, 54 are corrected in accordance with the supplied amounts for correction, as described above. The image to be represented on the display 20 also varies in accordance with this correction or the command entered by the operator.

If the operator finds that the image in the frame of interest is appropriate (the result of the verification is OK), he or she gives a command for print start using the keyboard 18a or the mouse 18b. Thus, the image processing conditions are finalized, and the film carrier 30 starts to transport the film F in the same direction as prescan at a speed adapted for fine scan, whereby fine scan of this frame is started under the reading conditions previously set.

If no verification is to be performed, the image processing conditions are finalized at the point of time when the parameter coordinating subsection 76 ends setting of the image processing conditions in the image processing subsection 54 of the fine scanned data processing section 46. Thus, fine scan is started. Whether verification should be performed or not is preferably determined in appropriately selectable modes.

When the fine scanned image data is sent to the fine scan memory 42, the image data of each frame is sequentially read out by the fine scanned data processing section 46 and processed in the image processing subsection 54 under the corresponding image processing conditions.

The image data processed in the processing subsection 54 is output to the deficient pixel correcting subsection 56. When the information about the deficient pixels is output from the detecting subsection 78, the deficient pixel correcting subsection 56 uses the image data of the surrounding pixels to correct the image data of the deficient pixels, thereby producing image data in which the scratch and foreign matter have been corrected.

The image data processed in the deficient pixel correcting subsection 56 is then converted in the image data transforming subsection 58 into output image data, which is then output into the image output machine 16.

The image output machine 16 comprises a printer (exposing apparatus) in which a light-sensitive material (photographic paper) is exposed in accordance with the supplied image data to record a latent image and a processor (developing apparatus) in which the exposed light-sensitive material is subjected to development and other specified processing to output a (finished) print.

To give one example of the printer's operation, the light-sensitive material is cut to a specified length in accordance with the size of the final print; thereafter, the printer records a back print and three light beams for exposure to R, G and B in accordance with the spectral sensitivity characteristics of the light-sensitive material are modulated in accordance with the image data output from the processing apparatus 14; the three modulated light beams are deflected in the main scanning direction while, at the same time, the light-sensitive material is transported in the auxiliary scanning direction perpendicular to the main scanning direction so as to record a latent image thereon by two-dimensional scan exposure with the light beams; the light-sensitive material including the latent image is supplied to the processor, where it is subjected to a wet development process comprising color development, bleach-fixing and rinsing, then dried to produce a print; a plurality of prints thus produced, for example those corresponding to a film roll are sorted and stacked.

In the above embodiment, as the reading light incident on the film F, the first prescan and the second prescan use the substantially parallel light incident at right angles with the film face and substantially perfectly diffused light, respectively. However, the present invention is not limited to this case and may also use the substantially perfectly diffused light and the substantially parallel light incident at right angles with the film face as the reading light for the first prescan and the reading light for the second prescan, respectively, so that the deficient pixels derived from a scratch and any foreign matter can be detected from the image data obtained.

Figure 5:
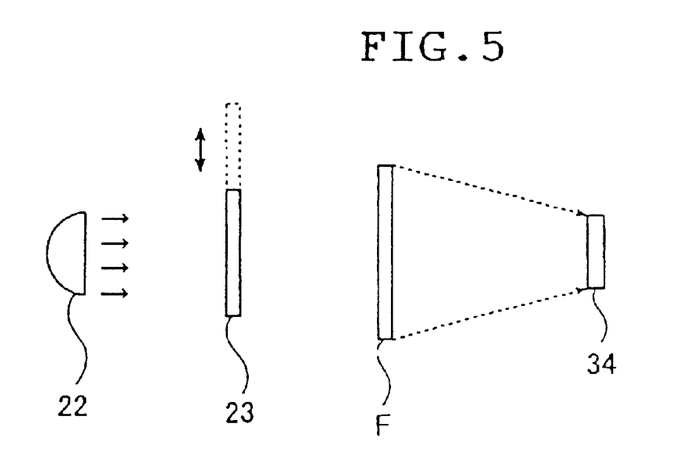
FIG. 5 is a conceptual view illustrating another method of changing reading light in the image reading apparatus according to the above embodiment.

Instead of interchanging the two light sources 22, 24, the layout shown in FIG. 5 is also possible in which the first light source 22 issuing the substantially parallel reading light incident at right angles with the film face is only provided, and in which a diffusing device 23 capable of converting the reading light from the above light source 22 to the substantially perfectly diffused light is provided between the first light source 22 and the film F. The diffusing device 23 used in the present invention may include a diffusing plate such as a frosted glass.

Figure 6:
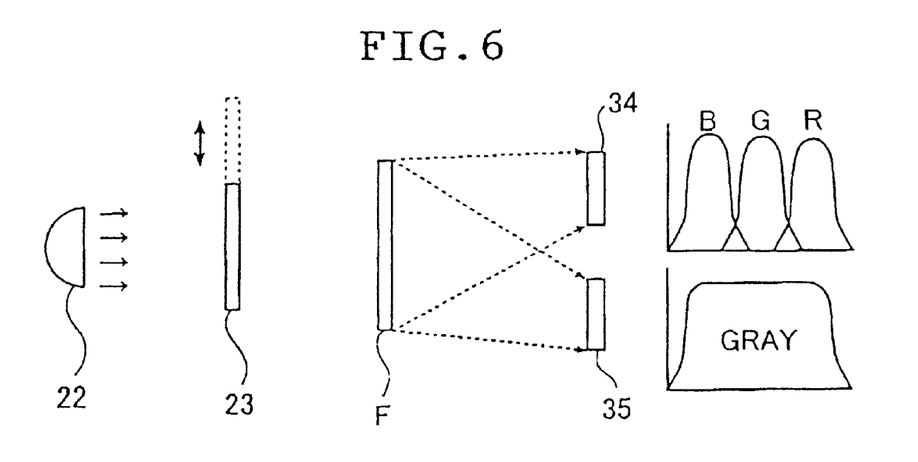
FIG. 6 is a conceptual view illustrating a method of detecting the reading light (projected light) in the image reading apparatus according to the above embodiment.

Further, in the above embodiment, the transmitted image data obtained by allowing the reading lights of different states of diffusion to be incident on and pass through the film F is read with the same image sensor 34. However, the present invention is not limited to this method and the image data may be read with two or more image sensors that have different spectral sensitivities in accordance with the reading lights of the respective states of diffusion. For example, a method as shown in FIG. 6 may be adopted in which the color image sensor 34 for three R, G and B colors to obtain color image information is used for reading with the substantially parallel light, and a monochrome sensor 35 for reading with the diffused light. This method covers the reduction in the quantity of light that occurs in a high state of diffusion, namely when reading with the diffused light, whether a plurality of light sources having the same outputs are used in general or whether a light source is used together with a diffusing plate.

The state of the projected light scattered by a slight scratch on the film F, improvement in the quantity of the light transmitted through the film F due to a deep scratch of the film F, and the reduction in the quantity of transmitted light due to light blocking caused by a foreign matter adhered to the film F are different in degree depending on the quantity of light of the reading light. Therefore, when reading the image with reading light of different quantities, the amounts of change in the outputs from the image sensor or in the image data follow the changes in the quantity of light of the reading light in the portion having no scratch or foreign matter, but provide different results in the portion having a scratch or foreign matter.

Under the circumstances, image reading of the film F is performed with reading light of different quantities of light to thereby detect the deficient pixels in the same manner, making the use of the abrupt change of the image data and the amounts of change of the two image data.

That is, when reading with the reading light in a state near to parallel light having low degree of diffusion, the efficiency for light utilization is increased. Then, the light source requires less power, but the scratch and the foreign matter on the film are more easily marked. In contrast, when reading with the reading light in a state having high degree of diffusion, the efficiency for light utilization is decreased. Then, the power of the light source needs be increased to obtain a high quality image, but the scratch and the foreign matter on the film is less marked, because the light is diffused in the portions having the scratch and the foreign matter.

Under the circumstances, the present invention compares, as mentioned above, the image (image data) or the reading results obtained from the two reading lights of different states of diffusion, thereby detecting whether the scratch and foreign matter exist or not, and further specifying the positions and regions of the detected scratch and foreign matter. These regions are then corrected (removed) by image processing. However, this is not the sole case of the invention, and any number of reading lights may be used, if two or more reading lights used have different states of diffusion. Two or more reading results of the same image that correspond to the two or more reading lights respectively may be used to detect the scratch and the foreign matter.

The quality of the read image (data) need be only on a level sufficient to enable detection and correction of the scratch and foreign matter, because reading of film images with the reading light having higher degree of diffusion is performed in the present invention to detect and correct the scratch and foreign matter. Then, when using at least two light sources, the power of the light source for the reading light having higher degree of diffusion can be reduced and the optical charge storage time of the image sensor can be also shortened, which enables speed-up of image reading with the reading light having higher degree of diffusion. Further, the present invention performs detection and correction of the scratch and foreign matter based on whether the image (image data) read with at least two reading lights of different states of diffusion has differences especially in terms of luminance component, specifically based on the degree of the differences. Hence, image reading with the reading light in a state having higher degree of diffusion may be performed on the black-and-white image (data) with the monochrome sensor, as described above. Thus, when reading the black-and-white image (data) with the monochrome sensor, similar effects including reduction of the light source power and shortening of the storage time in the image sensor can be further expected.

While the image reading method and apparatus of the present invention have been described above in detail, it should be noted that the invention is by no means limited to the foregoing embodiments and various improvements and modifications may of course be made without departing from the scope and spirit of the invention. In the above embodiment, the deficient pixels are detected for example using the prescanned data. However, fine scanned data may be used for detection. In the latter case, reading may be performed under the conditions equivalent to those for fine scan while adopting different incident angle and light intensity for the reading light.

As described above in detail, in the digital image reading method and apparatus that are used in the photoprinter or the like, the invention is capable of surely detecting a scratch or foreign matter on the film and correcting it as required, whereupon high-quality images having no image deterioration due to the scratch or foreign matter can be reproduced in a consistent manner.

What is claimed is:

1. An image reading method comprising the steps of:
    allowing reading light to be incident on and pass through a film to obtain projected light; and
    reading the thus obtained projected light photoelectrically to perform reading of an image recorded on said film,
    wherein at least one of a scratch and a foreign matter on said film is detected based on at least two reading results obtained by reading said same image independently with at least two types of reading light in different states of diffusion and said at least two reading results are obtained by reading said image photoelectrically using a plurality of sensors having different spectral sensitivities in accordance with the states of diffusion of said at least two types of reading light in the different states of diffusion.

2. The image reading method according to claim 1, wherein said at least two types of reading light in the different states of diffusion include a type of reading light in a state near to parallel light and another type of reading light in a state near to perfectly diffused light.

3. The image reading method according to claim 1, wherein said scratch and said foreign matter are a scratch and a foreign matter in an area of image recorded on said film.

4. The image reading method according to claim 1, wherein said at least two types of reading light in the different states of diffusion include at least two types of reading light that are issued from at least two light sources, respectively, and in which said states of diffusion are different from each other.

5. The image reading method according to claim 1, wherein said at least two types of reading light in the different states of diffusion include a type of reading light issued from a light source and another type of reading light obtained by diffusing said type of reading light issued from said light source by means of a diffusing device so that said states of diffusion are different from each other.

6. An image reading apparatus which allows reading light to be incident on and pass through a film to obtain projected light and reads the thus obtained projected light photoelectrically to perform reading of an image recorded on said film, comprising:
    a light-issuing device for allowing at least two types of reading light in different states of diffusion to be incident on said film;
    an image reading device for reading photoelectrically the projected light bearing the image recorded on said film as obtained from said at least two types of reading light in the different states of diffusion that have been issued from said light-issuing device and passed through said film; and
    a detecting device for detecting at least one of a scratch and a foreign matter on said film based on at least two reading results obtained by reading the same image independently with said at least two types of reading light in the different states of diffusion by means of said image reading device, and wherein said image reading device has a plurality of sensors having different spectral sensitivities and wherein the plurality of sensors having the corresponding spectral sensitivities are used in accordance with the states of diffusion of said at least two types of reading light in the different states of diffusion to obtain said at least two reading results.

7. The image reading apparatus according to claim 6, wherein said at least two types of reading light in the different states of diffusion include a type of reading light in a state near to parallel light and another type of reading light in a state near to perfectly diffused light.

8. The image reading apparatus according to claim 6, wherein said scratch and said foreign matter are a scratch and a foreign matter in the image recorded on said film.

9. The image reading apparatus according to claim 6, wherein said light-issuing device includes at least two light sources that issue said at least two types of reading light in the different states of diffusion, respectively.

10. The image reading apparatus according to claim 6, wherein said light-issuing device includes a light source issuing a type of reading light and a changing device for changing said type of reading light issued from said light source so that said states of diffusion of said type of reading light and another type of reading light being produced are different from each other.

11. The image reading apparatus according to claim 6, wherein one of said plurality of sensors is a monochrome sensor.

12. The image reading apparatus according to claim 6, wherein said image reading device obtains said at least two reading results by prescan for reading the image recorded on said film at low resolution.

13. The image reading apparatus according to claim 6, wherein said detecting device uses said at least two reading results to detect, as said at least one of the scratch and the foreign matter, a region that has a difference between image data read with a type of reading light of lower diffusion and image data read with another type of reading light of higher diffusion in said at least two types of reading light in the different states of diffusion.

14. The image reading apparatus according to claim 6, which further includes a deficient pixel correcting device for correcting, as deficient pixels, a region corresponding to said at least one of the scratch and the foreign matter detected by said detecting device.

15. The image reading apparatus according to claim 14, wherein said deficient pixel correcting device performs correction using surrounding image data of said deficient pixels.

16. The image reading apparatus according to claim 14, wherein said deficient pixel correcting device performs at least one of a method of substituting image data of said deficient pixels by the surrounding image data of said deficient pixels, a method of substituting the image data of said deficient pixels by image data calculated by interpolation with the surrounding image data of said deficient pixels, and a method of using, as the image data of said deficient pixels, image data read with reading light of higher state of diffusion in said at least two types of reading light in the different states of diffusion.

* * * * *